US009224769B2

(12) United States Patent
Park et al.

(10) Patent No.: US 9,224,769 B2
(45) Date of Patent: Dec. 29, 2015

(54) PIXEL DEVICE, AND RADIATION DETECTING MODULE AND APPARATUS HAVING THE SAME

(75) Inventors: Jae-chul Park, Gyeonggi-do (KR); Young Kim, Gyeonggi-do (KR); Chang-jung Kim, Gyeonggi-do (KR)

(73) Assignees: Samsung Electronics Co., Ltd., Gyeonggi-do (KR); Samsung Display Co., Ltd., Gyeonggi-do (KR)

( * ) Notice: Subject to any disclaimer, the term of this patent is extended or adjusted under 35 U.S.C. 154(b) by 745 days.

(21) Appl. No.: 13/433,985

(22) Filed: Mar. 29, 2012

(65) Prior Publication Data

US 2012/0318989 A1    Dec. 20, 2012

(30) Foreign Application Priority Data

Jun. 16, 2011  (KR) .................. 10-2011-0058639

(51) Int. Cl.
| | | |
|---|---|---|
| G01T 1/20 | (2006.01) | |
| H01L 27/146 | (2006.01) | |
| H04N 5/369 | (2011.01) | |
| G01T 1/208 | (2006.01) | |
| A61B 6/03 | (2006.01) | |

(52) U.S. Cl.
CPC .... *H01L 27/14609* (2013.01); *H01L 27/14663* (2013.01); *H04N 5/3698* (2013.01); *A61B 6/037* (2013.01); *G01T 1/2006* (2013.01); *G01T 1/208* (2013.01); *G01T 1/2018* (2013.01); *H01L 27/14618* (2013.01); *H01L 2924/0002* (2013.01)

(58) Field of Classification Search
CPC ...... G01T 1/2006; G01T 1/2018; G01T 1/208
USPC .......................................... 250/366
See application file for complete search history.

(56) References Cited

U.S. PATENT DOCUMENTS

| | | | | |
|---|---|---|---|---|
| 4,972,255 | A | * | 11/1990 | Suzuki et al. ............... 358/513 |
| 6,157,022 | A | * | 12/2000 | Maeda et al. ............. 250/214 R |
| 7,402,788 | B2 | * | 7/2008 | McVey ..................... 250/214 R |
| 7,897,906 | B2 | * | 3/2011 | Deschamps ............... 250/214 R |
| 8,222,589 | B2 | * | 7/2012 | Wang ....................... 250/214 R |
| 8,476,594 | B2 | * | 7/2013 | Frach et al. .............. 250/363.03 |
| 2006/0202129 | A1 | * | 9/2006 | Niclass et al. ............ 250/370.14 |
| 2008/0290259 | A1 | * | 11/2008 | Mathewson et al. ...... 250/214 R |
| 2011/0108702 | A1 | * | 5/2011 | Jackson et al. ............... 250/207 |
| 2011/0133059 | A1 | * | 6/2011 | Kim et al. ................ 250/214 R |

FOREIGN PATENT DOCUMENTS

| | | |
|---|---|---|
| JP | 2006048011 A | 2/2006 |
| JP | 2006278361 A | 10/2006 |
| KR | 100658672 B1 | 12/2006 |
| KR | 20070035388 A | 3/2007 |

* cited by examiner

*Primary Examiner* — Christine Sung
(74) *Attorney, Agent, or Firm* — Harness, Dickey & Pierce, P.L.C.

(57) ABSTRACT

A pixel device having an improved energy resolution includes at least one photodiode and at least one voltage supply unit for applying a voltage to the photodiode. The pixel device includes a voltage storage unit and a voltage adjusting unit. In a precharge mode, the voltage storage unit stores a first anode voltage. In a sensing mode, the voltage adjusting unit adjusts a second anode voltage of the anode of the photodiode to be the same as the first anode voltage stored in the voltage storage unit.

18 Claims, 11 Drawing Sheets

PIXEL DEVICE, AND RADIATION DETECTING MODULE AND APPARATUS HAVING THE SAME

CROSS-REFERENCE TO RELATED APPLICATIONS

This application claims priority under 35 U.S.C. §119 to Korean Patent Application No. 10-2011-0058639, filed on Jun. 16, 2011, in the Korean Intellectual Property Office, the disclosure of which is incorporated herein in its entirety by reference.

BACKGROUND

1. Field

Example embodiments relate to pixel devices, radiation detecting modules, and radiation detecting apparatuses, and for example, to variation-adaptive pixel devices, and radiation detecting modules and apparatuses having the pixel devices.

2. Description of the Related Art

Positron emission tomography (PET) apparatuses are radiation detecting apparatuses capable of obtaining a PET image by combining a metabolite, e.g., glucose with a radio-isotope for emitting positrons, injecting the metabolite into a human body, and observing biochemical changes occurring in the body.

PET apparatuses are used to assist in early detection of cancer by taking advantage of the phenomenon that cancer cells exhibit a higher intake and metabolism of glucose than that seen in normal cells. In more detail, fluorodeoxyglucose (FDG), which is a glucose-like substance, is combined with an isotope for emitting positrons and injected into a human body. The PET apparatus may be used to observe cancer cells taking in the FDG-isotope combination. PET apparatuses may detect molecular-level changes in the human body that were hard to detect with existing imaging, and thus enable early detection of cancer.

SUMMARY

Example embodiments provide pixel devices adaptive to a variation in process conditions or operation temperature, or to stress caused by long-term driving, and radiation detecting modules and apparatuses having the same.

Additional aspects will be set forth in part in the description that follows and, in part, will be apparent from the description, or may be learned by practice of the example embodiments.

At least one example embodiment provides a pixel device. The pixel device includes at least one photodiode and at least one voltage supply unit for applying a voltage to the photodiode, and including a voltage storage unit and a voltage adjusting unit. In a precharge mode, the voltage storage unit stores a first anode voltage. In a sensing mode, the voltage adjusting unit adjusts a second anode voltage of the anode of the photodiode to be the same as the first anode voltage stored in the voltage storage unit.

The voltage storage unit may comprise a capacitor. In the precharge mode, the voltage storage unit may be connected to an anode of the photodiode. The first anode voltage may be a breakdown voltage of the photodiode.

According to at least some example embodiments, the pixel device may include a quenching unit connected to a cathode of the at least one photodiode for allowing the photodiode to transist to a quiescent state. The pixel device may include a readout unit connected to the cathode of the at least one photodiode to counting transitions of the at least one photodiode.

the pixel device may further include a first switch connected between the anode of the at least one photodiode and the voltage storage unit. The first switch may be turned on in the precharge mode and may be turned off in the sensing mode.

According to example embodiments, the pixel device may further include a second switch connected between the voltage storage unit and the voltage adjusting unit. The second switch may be turned off in the precharge mode and may be turned on in the sensing mode.

The voltage supply unit may include a closed loop circuit.

According to example embodiments, the voltage adjusting unit may include a first comparator including a first terminal connected to the voltage storage unit and for receiving the first anode voltage; a second terminal connected to the anode of the photodiode and for receiving the second anode voltage; and a first output terminal for comparing signals of the first and second terminals and outputting a comparison result; and a transistor including a gate connected to the first output terminal of the first comparator; a source connected to a ground; and a drain connected to the anode of the photodiode.

The voltage adjusting unit may further include a third switch connected between the gate of the transistor and the first output terminal of the first comparator. The third switch may be turned off in the precharge mode and may be turned on in the sensing mode.

According to example embodiments, the pixel device may further include a second comparator. The second comparator may include a third terminal connected to the cathode of the at least one photodiode. The second comparator may include a fourth terminal for receiving a reference voltage. The second comparator may also include a second output terminal for comparing signals of the third and fourth terminals and outputting a comparison result. The pixel device may also include a fourth switch connected between the gate of the transistor and the second output terminal of the second comparator. The fourth switch may be turned on in the precharge mode and may be turned off in the sensing mode.

According to at least some example embodiments, the pixel device may include a plurality of microcells and, the at least one photodiode may include a plurality of photodiodes. The plurality of photodiodes may be individually included in the plurality of microcells.

The at least one voltage supply unit may include a plurality of voltage supply units, and the plurality of voltage supply units may be individually included in the plurality of microcells.

The at least one voltage supply unit may be a single voltage supply unit, and the single voltage supply unit may be connected to the plurality of microcells and may apply a voltage to the plurality of photodiodes.

At least one other example embodiment provides a radiation detecting module. The radiation detecting module includes a scintillator for receiving radiation and generating photons and a plurality of pixel devices for receiving the photons generated by the scintillator. Each of the plurality of pixel devices may include at least one photodiode and at least one voltage supply unit for applying a voltage to the photodiode, and including a voltage storage unit and a voltage adjusting unit. In a precharge mode, the voltage storage unit stores a first anode voltage. In a sensing mode, the voltage adjusting unit adjusts a second anode voltage of the anode of the photodiode to be the same as the first anode voltage stored in the voltage storage unit.

The radiation detecting module may further include a printed circuit board (PCB) for mounting the semiconductor chip and including at least one power pin for providing a supply voltage to the plurality of pixel devices. The plurality of pixel devices may be integrated on the semiconductor chip in the form of an array.

The at least one power pin may be a single power pin, and the single power pin may be electrically connected to and may provide a supply voltage to the plurality of pixel devices. In the precharge mode, the voltage storage unit may be connected to an anode of the photodiode.

At least one other example embodiment provides a radiation detecting apparatus. The radiation detecting apparatus may include an image region for accommodating a target object to capture an image of the target object; a plurality of radiation detecting modules surrounding the image region, for receiving radiation from the target object, and for transforming the radiation into electrical signals; and an image processing unit for generating the image of the target object based on the electrical signals. Each of the radiation detecting modules may include a scintillator for receiving radiation and generating photons and a plurality of pixel devices for receiving the photons generated by the scintillator. Each of the plurality of pixel devices may include at least one photodiode and at least one voltage supply unit. The voltage supply unit for applying a voltage to the photodiode, and including a voltage storage unit and a voltage adjusting unit. In a precharge mode, the voltage storage stores a first anode voltage. In a sensing mode, the voltage adjusting unit adjusts a second anode voltage of the anode of the photodiode to be the same as the first anode voltage stored in the voltage storage unit.

BRIEF DESCRIPTION OF THE DRAWINGS

These and/or other aspects will become apparent and more readily appreciated from the following description of example embodiments, taken in conjunction with the accompanying drawings in which.

DETAILED DESCRIPTION

Example embodiments will now be described more fully with reference to the attached drawings, in which example embodiments are shown.

Example embodiments may, however, be embodied in many different forms and should not be construed as being limited to the embodiments set forth herein; rather, these embodiments are provided so that this disclosure will be thorough and complete, and will fully convey the concept of example embodiments to one of ordinary skill in the art. Like reference numerals in the drawings denote like elements, and thus their description will be omitted.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers indicate like elements throughout. As used herein the term "and/or" includes any and all combinations of one or more of the associated listed items. Other words used to describe the relationship between elements or layers should be interpreted in a like fashion (e.g., "between" versus "directly between," "adjacent "versus "directly adjacent," "on" versus "directly on").

The terminology used herein is for the purpose of describing particular embodiments and is not intended to limit example embodiments. As used herein, the singular forms "a", "an", and "the" are intended to include the plural forms as well, unless the context clearly indicates otherwise. It will be further understood that the terms "comprises," "comprising," "includes" and/or "including," when used in this specification, specify the presence of stated features, integers, steps, operations, elements, and/or components, but do not preclude the presence or addition of one or more other features, integers, steps, operations, elements, components, and/or groups thereof. As used herein, the term "and/or" refers to one of or a combination of at least two listed items.

It will be understood that, although the terms "first," "second," "third," etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Example embodiments are described herein with reference to schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein, but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Figure 1:
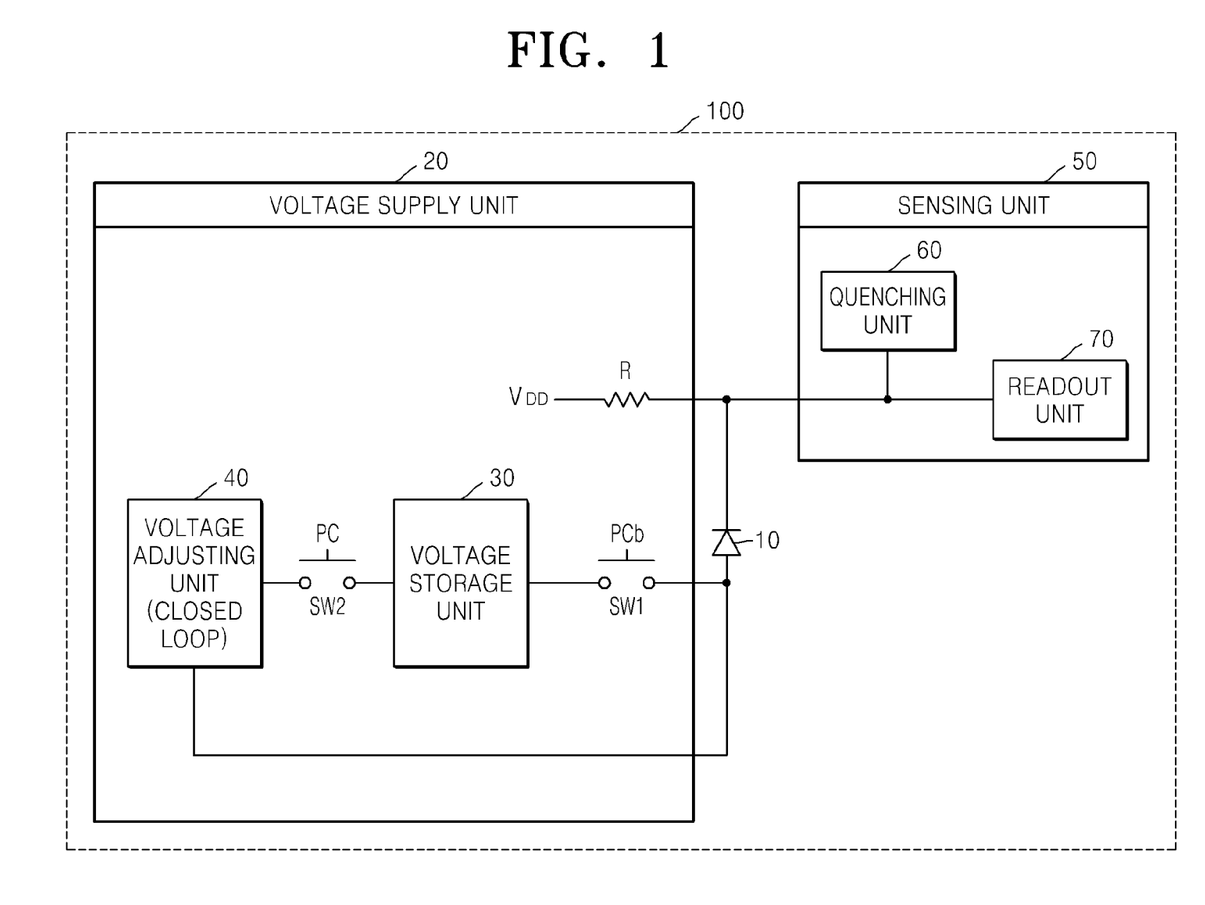
FIG. 1 is a block diagram of a pixel device according to an example embodiment.

FIG. 1 is a block diagram of a pixel device 100 according to example embodiments.

Referring to FIG. 1, the pixel device 100 may be a silicon photomultiplier (SiPM) and may include a photodiode 10, a voltage supply unit 20, and a sensing unit 50. The pixel device 100 may be a semiconductor light sensor that operates in a restricted Geiger mode. The pixel device 100 may be used in a positron emission tomography (PET) apparatus. The pixel device 100 may include more than 500 microcells (not shown, see reference numeral 90 in FIG. 9), and one microcell may have a size of about 20 micrometers. Each microcell may independently detect and amplify photons. As photons enter each microcell, electron-hole pairs may be generated due to an electric field in the pixel device 100, amplification may occur, and a signal may be generated and output by each microcell. The output signal of the pixel device 100 may be obtained by combining the signals of all the microcells.

The photodiode 10 may generate a current based on photons resolved by a scintillator (not shown). A plurality of photodiodes 10 may be individually included in the microcells. The photodiode 10 may be, in a least one non-limiting example, an avalanche photodiode.

The voltage supply unit 20 may be a circuit for applying a breakdown voltage to the photodiode 10, and may include a voltage storage unit 30 and a voltage adjusting unit 40.

The voltage storage unit 30 may operate in a precharge mode. The voltage storage unit 30 may be connected to an anode of the photodiode 10, and the voltage storage unit 30 may store a first anode voltage. The first anode voltage may correspond to a breakdown voltage of the photodiode 10, and thus the voltage storage unit 30 may store the breakdown voltage. The voltage storage unit 30 may include a capacitor (not shown).

The voltage adjusting unit 40 may operate in a sensing mode, and the voltage adjusting unit 40 may be connected between the anode of the photodiode 10 and the voltage storage unit 30. The voltage adjusting unit 40 may adjust a second anode voltage (e.g., a bias voltage) at the anode of the photodiode 10 to match the first anode voltage, which is stored in the voltage storage unit 30. The voltage adjusting unit 40 may include a feedback circuit, e.g., a closed loop circuit, for use in matching the second anode voltage to the stored first anode voltage of the photodiode 10.

In order to allow the voltage storage unit 30 to operate in the precharge mode and to allow the voltage adjusting unit 40 to operate in the sensing mode, the voltage supply unit 20 may further include a first switch SW1 and a second switch SW2.

The first switch SW1 may be connected between the anode of the photodiode 10 and the voltage storage unit 30. The first switch SW1 may be turned on in the precharge mode based upon an first operation signal PCb. The switch SW1 may be turned off in the sensing mode. In the precharge mode, the first switch SW1 may electrically connect the anode of the photodiode 10 to the voltage storage unit 30, and thus the first anode voltage of the photodiode 10 may be stored in the voltage storage unit 30.

The second switch SW2 may be connected between the voltage storage unit 30 and the voltage adjusting unit 40. The second switch SW2 may be turned off in the precharge mode, and turned on in the sensing mode based upon a second operation signal PC. In the sensing mode, the second switch SW2 may electrically connect the voltage storage unit 30 to the voltage adjusting unit 40, and thus the voltage adjusting unit 40 may use the first anode voltage stored in the voltage storage unit 30.

The sensing unit 50 may be connected to the photodiode 10. The sensing unit 50 may include a quenching unit 60 and a readout unit 70. The quenching unit 60 may be connected to a cathode of the photodiode 10, and may allow the photodiode 10 to transition from a breakdown state to a quiescent state. The readout unit 70 may be connected to the cathode of the photodiode 10, and the readout unit 70 may count transitions of the photodiode 10.

As described above, according to example embodiments, the voltage supply unit 20 stores a breakdown voltage of the photodiode 10 in a precharge mode, and applies a certain breakdown voltage to the photodiode 10 in a sensing mode. In general, a variation in process conditions or operation temperature, or stress caused by long-term driving of the photodiode, may cause variation in the breakdown voltage of the photodiode. As such, a gain of the photodiode may be very sensitive to variations in conditions or to stress.

However, in the pixel device 100 according to example embodiments, the voltage supply unit 20 may apply a breakdown voltage to the photodiode 10. Accordingly, a gain of the photodiode 10 may be maintained at a constant level and an energy resolution may be improved.

Figure 2:
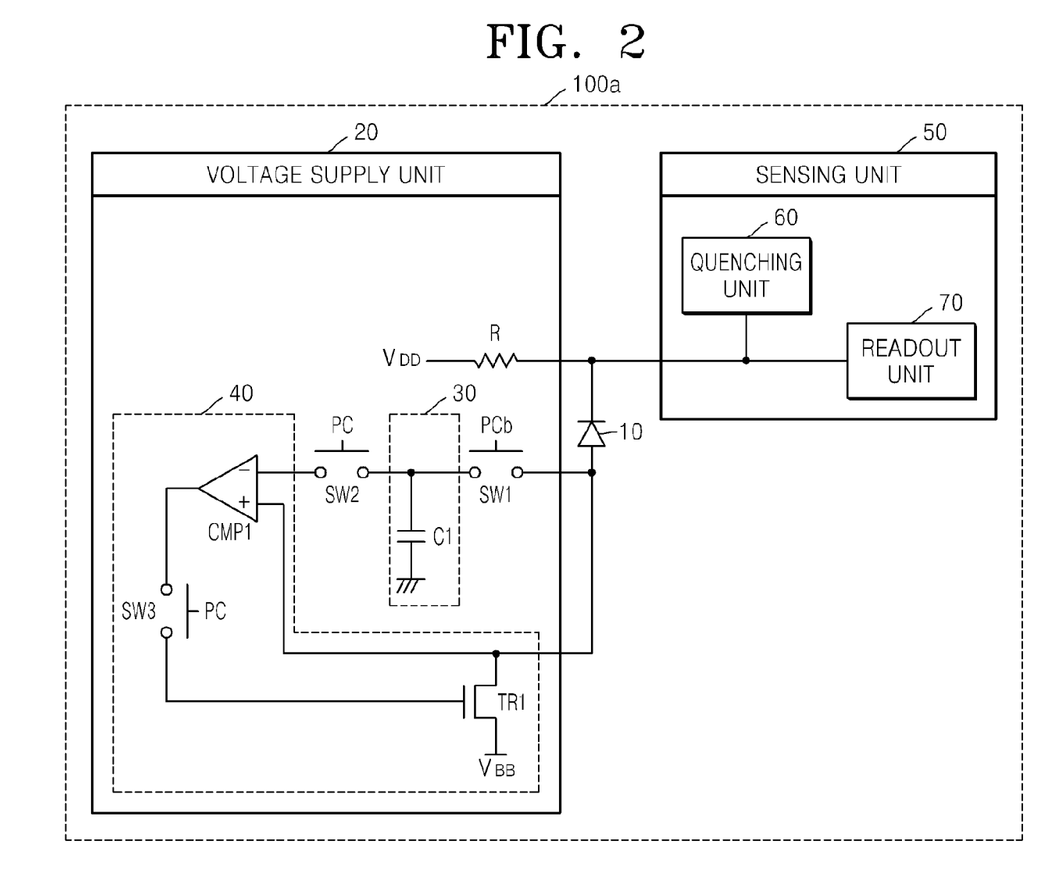
FIG. 2 is a circuit block diagram of a pixel device according to an example embodiment.

FIG. 2 is a circuit block diagram of a pixel device 100a according to example embodiments. The pixel device 100a may be modified from the pixel device 100 illustrated in FIG. 1. Elements already described with respect to FIG. 1 will not be described for the sake of brevity.

Referring to FIG. 2, the voltage storage unit 30 may include a capacitor C1. In the precharge mode, the first capacitor C1 is connected between ground and the anode of the photodiode 10. Accordingly, in the precharge mode, the capacitor C1 may store the first anode voltage of the anode of the photodiode 10. In the sensing mode, the first capacitor C1 is connected between the ground and the voltage adjusting unit 40. Accordingly, in the sensing mode, the first capacitor C1 may transfer the stored first anode voltage to the voltage adjusting unit 40.

The voltage adjusting unit 40 may include a first comparator CMP1, a first transistor TR1, and a third switch SW3. The first comparator CMP1 may include a first terminal connected to the voltage storage unit 30 for receiving the first anode voltage, a second terminal connected to the anode of the photodiode 10 for receiving the second anode voltage, and a first output terminal for comparing signals of the first and second terminals and outputting a comparison result. The first terminal may be an inverting terminal (−), and the second terminal may be a non-inverting terminal (+).

The first transistor TR1 may include a gate connected to the first output terminal of the first comparator CMP1, a source connected to the ground, and a drain connected to the anode of the photodiode 10. The first transistor TR1 may be an N-type transistor. The third switch SW3 may be connected between the gate of the first transistor TR1 and the first output terminal of the first comparator CMP1. Switch SW3 may be turned off in the precharge mode, and may be turned on in the sensing mode based upon operation signal PC. Operation of the voltage adjusting unit 40 in the sensing mode will now be described.

In the sensing mode, the first switch SW1 is turned off, and the second and third switches SW2 and SW3 are turned on. If the second anode voltage of the photodiode 10 varies due to, e.g., a variation in temperature, the second anode voltage is increased to be greater than the first anode voltage stored in the voltage storage unit 30, and the first comparator CMP1 may outputs a high-level signal from the first output terminal. Because the high-level signal is applied to the gate of the first transistor TR1, the transistor TR1, which may be an N-type transistor, is turned on. Accordingly, the second anode voltage is reduced and thereby adjusted to match the first anode voltage.

A variation in process conditions or operation temperature, or stress caused by long-term driving may vary a breakdown voltage of a photodiode. As described above, this variation may in turn cause a gain of the photodiode to vary. Variations in the gain of the photodiode may cause a dark count of a sensing circuit to be increased and thus an energy resolution of a pixel device may be lowered. However, in example embodiments, an anode of the photodiode 10 may be maintained at a certain voltage by using the voltage storage unit 30 and the voltage adjusting unit 40 as described in example embodiments above, and thus variations in a breakdown voltage of the photodiode 10 may be decreased or eliminated. Accordingly, a gain of the photodiode 10 may be maintained, a dark count may be reduced, and an energy resolution of a pixel device may be improved.

Figure 3:
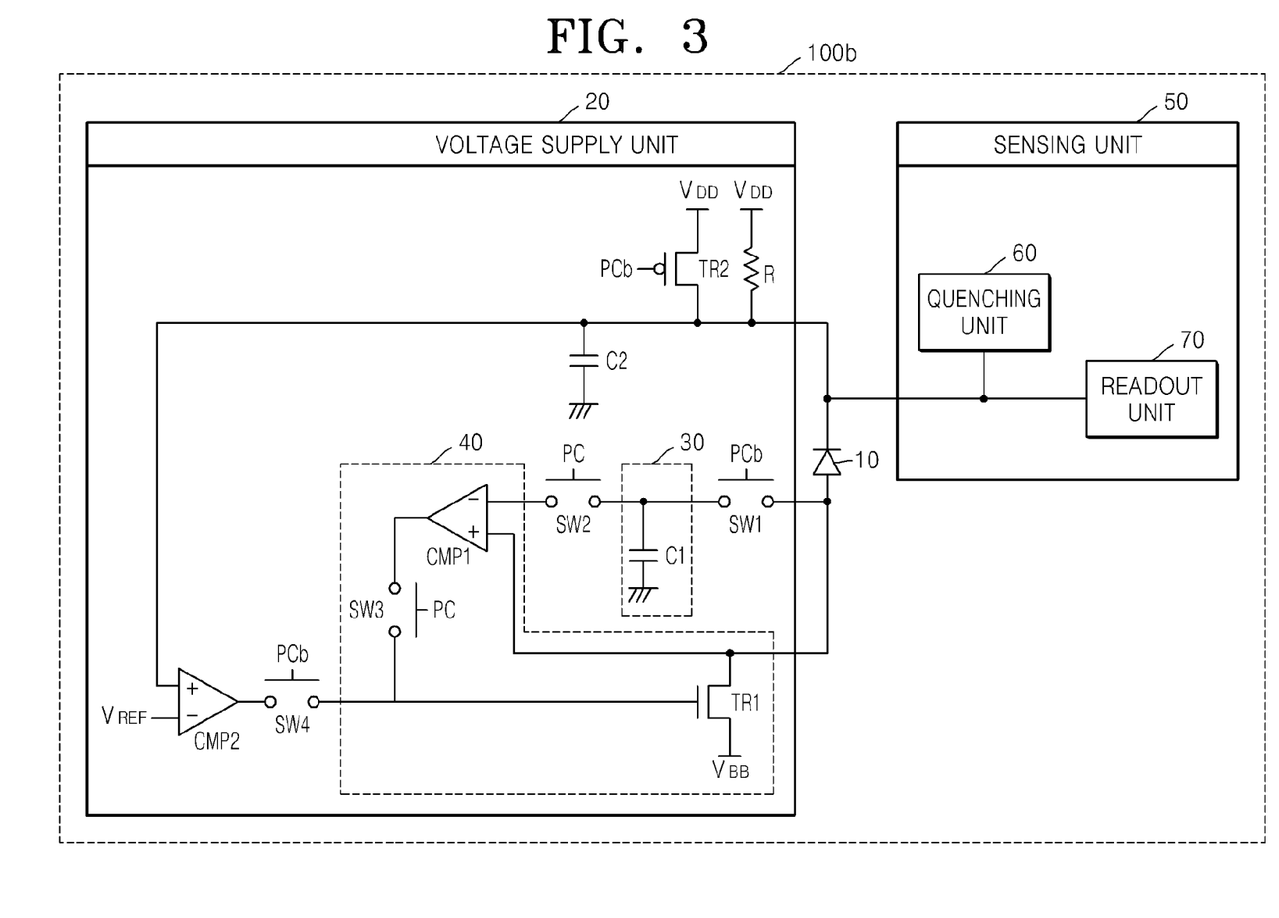
FIG. 3 is a circuit block diagram of a pixel device according to another example embodiment.
Figure 4:
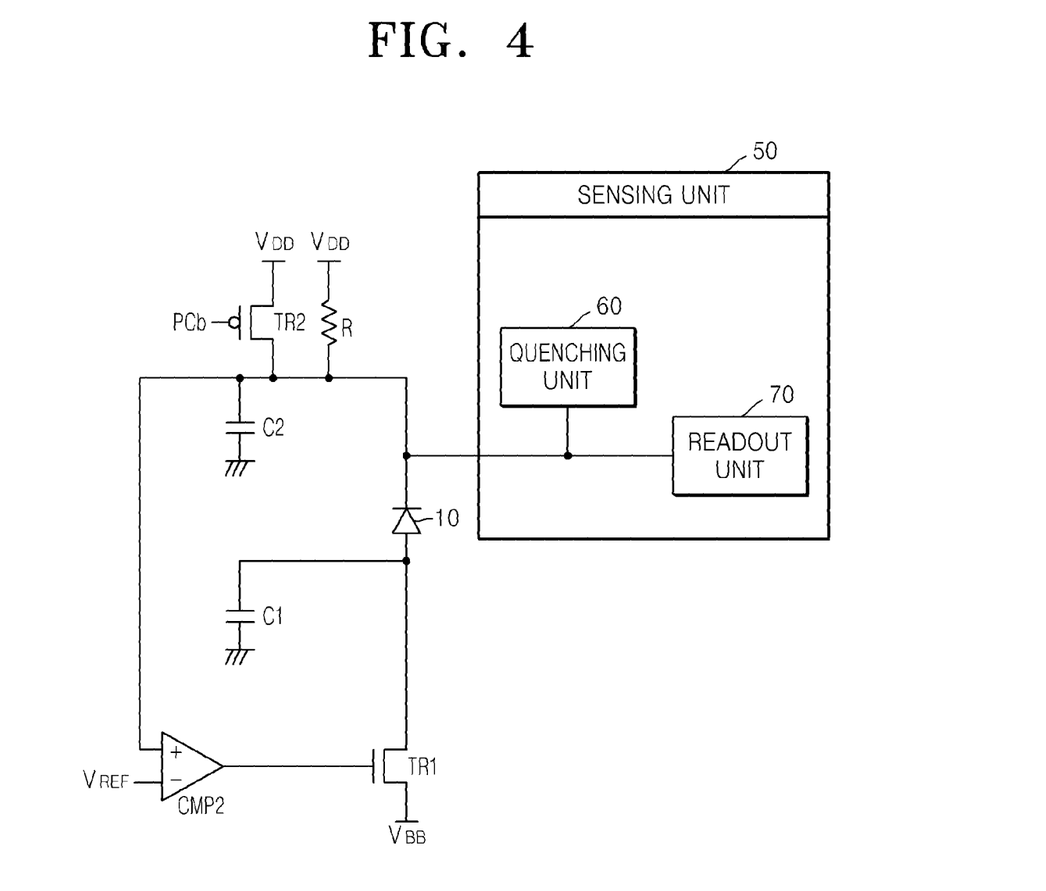
FIG. 4 is a circuit block diagram of the pixel device illustrated in FIG. 3 in a precharge mode.
Figure 5:
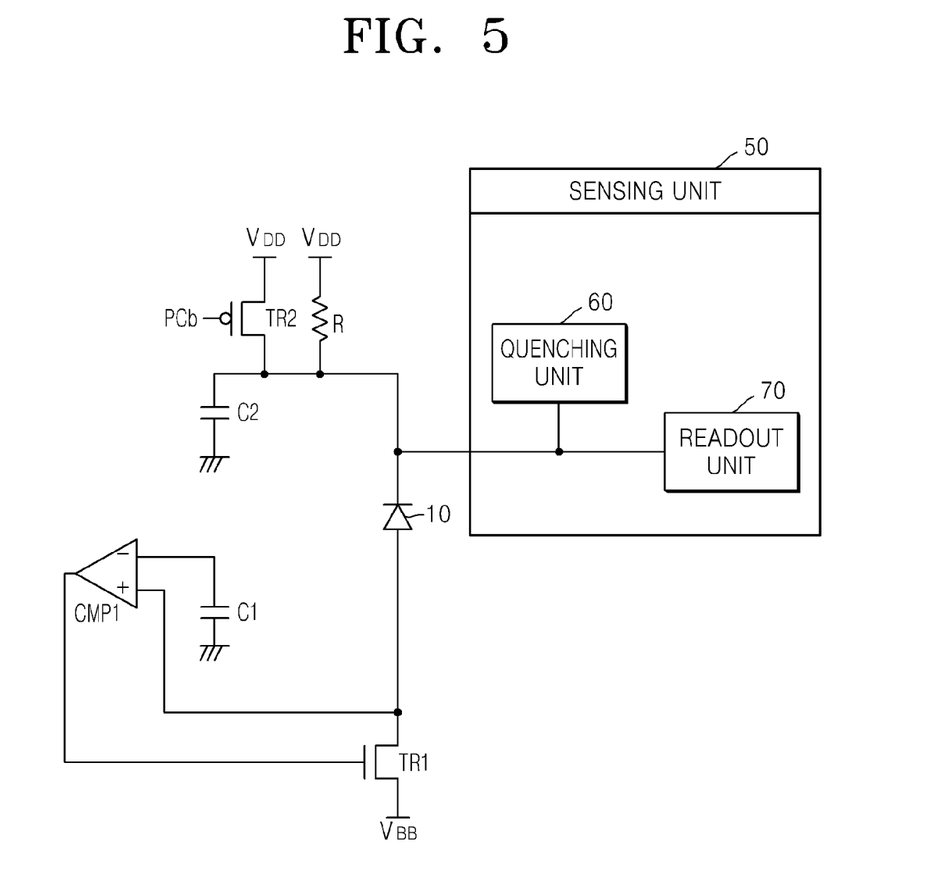
FIG. 5 is a circuit block diagram of the pixel device illustrated in FIG. 3 in a sensing mode.

FIG. 3 is a circuit block diagram of a pixel device 100b according to example embodiments. FIG. 4 is a circuit block diagram of the pixel device 100b illustrated in FIG. 3 when the pixel device 100b is in a precharge mode. FIG. 5 is a circuit block diagram of the pixel device 100b illustrated in FIG. 3 when the pixel device 100b is in a sensing mode. The pixel device 100b may be modified from the pixel device 100a illustrated in FIG. 2. Elements already described in previous figures will not be described for the sake of brevity.

Referring to FIG. 3, the voltage supply unit 20 may further include a second comparator CMP2, a fourth switch SW4, a second capacitor C2, a second transistor TR2, and a resistor R.

The second comparator CMP2 may include a third terminal connected to the cathode of the photodiode 10, a fourth terminal for receiving a reference voltage $V_{REF}$, and a second output terminal for comparing signals of the third and fourth terminals and outputting a comparison result. Also, the fourth switch SW4 may be connected between the gate of the first transistor TR1 and the second output terminal. Switch SW4 may be turned on in the precharge mode based upon the first operation signal PCb, and switch SW4 may be turned off in the sensing mode.

The second capacitor C2 may be connected between the cathode of the photodiode 10 and the ground. The second transistor TR2 may be a P-type transistor and may include a gate for receiving the first operation signal PCb, a source for receiving a supply voltage $V_{DD}$, and a drain connected to the cathode of the photodiode 10. The resistor R may be connected between a line of the supply voltage $V_{DD}$ and the cathode of the photodiode 10.

Referring to FIG. 4, in the precharge mode, the first operation signal PCb may be at a low level and the second operation signal PC may be at a high level. In this case, the second transistor TR2 is turned on, and a voltage of the cathode (i.e., a sensing node) of the photodiode 10 is at a high level due to the supply voltage $V_{DD}$. Because the second comparator CMP2 is connected to the first transistor TR1, the first anode voltage of the photodiode 10 is set by comparing the voltage of the cathode of the photodiode 10 to the reference voltage $V_{REF}$. The first anode voltage is stored in the first capacitor C1.

Referring to FIG. 5, in the sensing mode, the first operation signal PCb may be at a high level and the second operation signal PC may be at a low level. Operation of the circuit is the same as the operation described above in relation to FIG. 2. That is, the voltage adjusting unit 40 adjusts the second anode voltage of the photodiode 10 by using the first comparator CMP1 and the first transistor TR1 in such a way that the second anode voltage applied to a non-inverting terminal (+) of the first comparator CMP1 is the same as the first anode voltage applied to an inverting terminal (−) of the first comparator CMP1.

Figure 6:
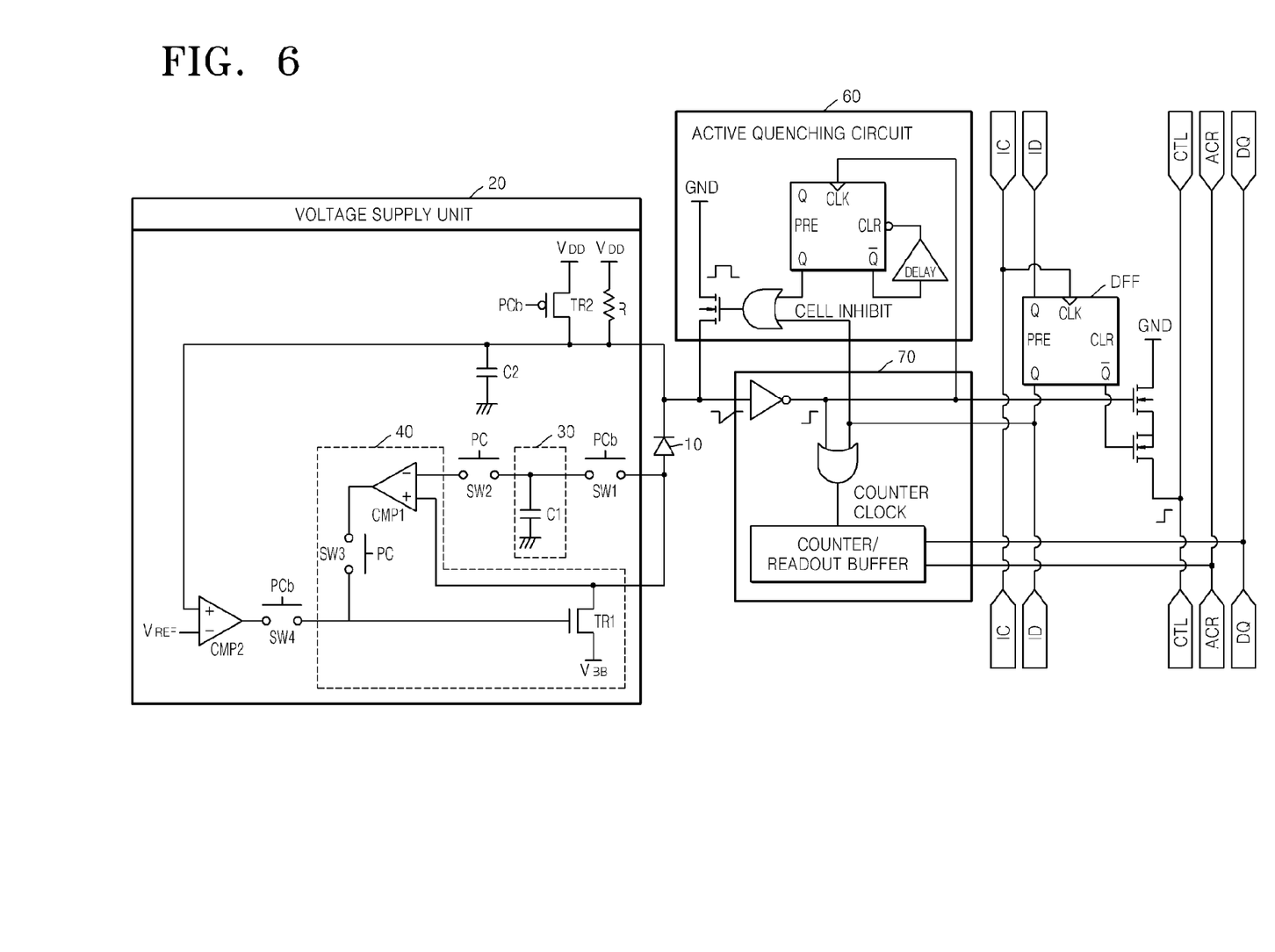
FIG. 6 is a circuit block diagram of a pixel device according to another example embodiment.

FIG. 6 is a circuit block diagram of a pixel device 100c according to example embodiments. The pixel device 100c may be modified from the pixel device 100b illustrated in FIG. 3. Repeated descriptions therebetween will not be provided here.

Referring to FIG. 6, details of the quenching unit 60 and the readout unit 70 are illustrated. If the photodiode 10 senses photons and generates a current, the current is discharged via the photodiode 10. The quenching unit 60 reduces a falling time and prevents or reduces a pile up phenomenon by providing and actively controlling an additional discharge path other than a discharge path via a diode.

If the photodiode 10 senses photons and generates a current, the readout unit 70 may count the photons by counting the transitions of the current. As described above in relation to FIG. 1, because the pixel device 100c may include a plurality of microcells and each of the microcells may include the photodiode 10 and the sensing unit 50, each of the microcells may count the photons. Accordingly, a total number of photons counted in the pixel device 100c is calculated, and an energy resolution is calculated based on the total number of photons.

Also, a time calculation function may be performed via a common trigger line (CTL). The time calculation function may be used to determine a time to transmit a signal from where radiation, e.g., a gamma ray, is emitted to a time to digital converting (TDC) circuit (not shown) on a printed circuit board (PCB). A time resolution may be determined based on the transmission time.

Furthermore, a failed-cell inhibiting function may be performed by using an inhibition clock IC, an inhibition data line ID, and a D flip-flop DFF. If an error occurs in the photodiode 10, the D flip-flop DFF may output an inhibition signal to prevent counting the number of photons sensed in a cell having an error.

The above features and functions are disclosed in U.S. patent application Ser. No. 11/467,670 (U.S. Pat. No. 7,723,694) entitled "Digital silicon photomultiplier for TOF-PET", and the above patent is incorporated herein in its entirety by reference.

Figure 7:
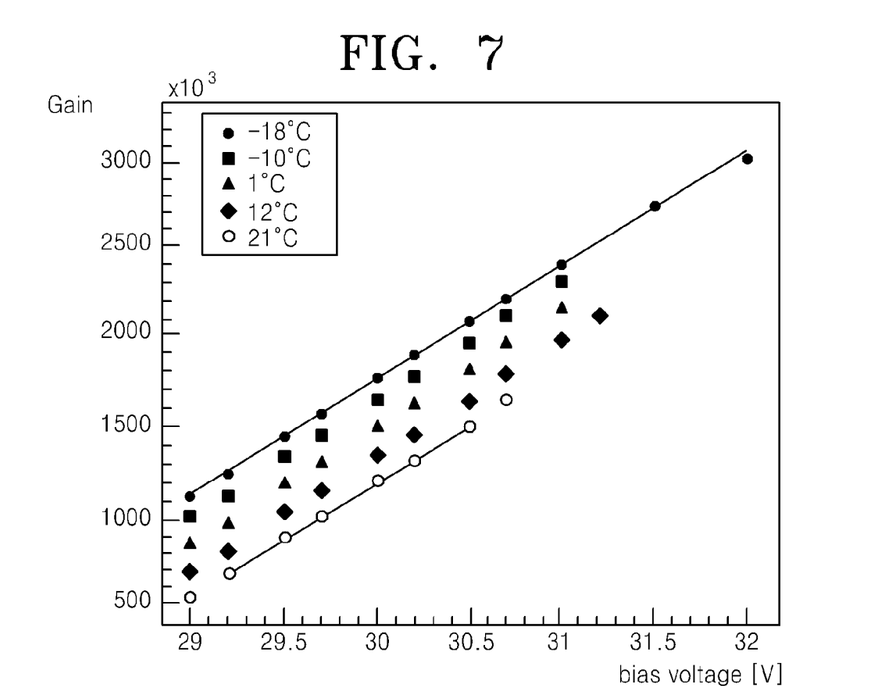
FIG. 7 is a graph showing example variations in gain according to variations in temperature of a pixel device according to example embodiments.
Figure 8:
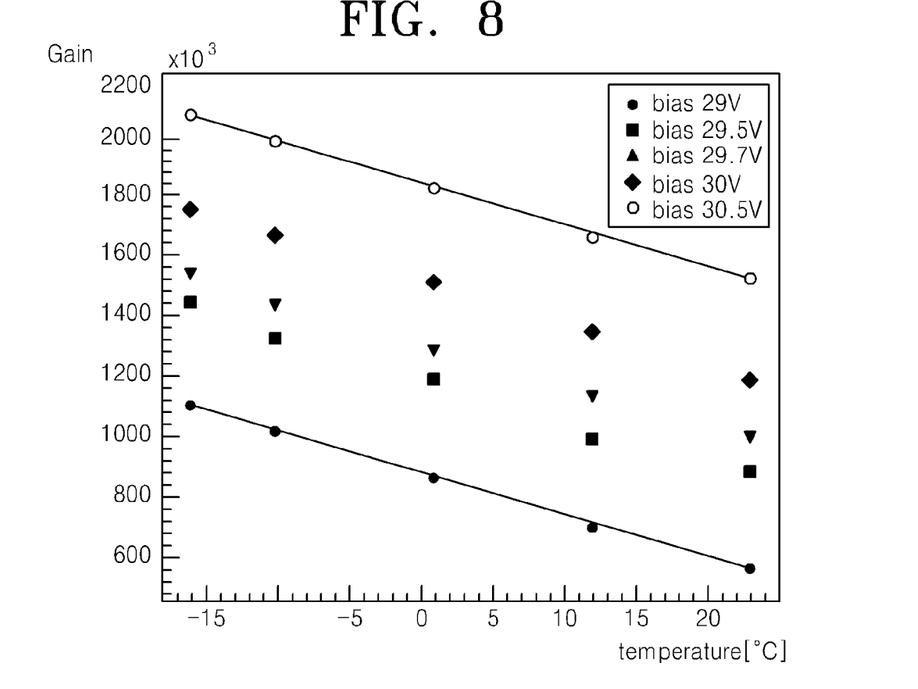
FIG. 8 is a graph showing example variations in gain according to variations in bias voltage of a pixel device according to example embodiments.

FIG. 7 is a graph showing variations in gain according to variations in temperature of a pixel device. FIG. 8 is a graph showing variations in gain according to variations in bias voltage of a pixel device.

Referring to FIGS. 7 and 8, a gain is reduced if the temperature of a pixel device (for example, a photodiode) is increased, because a breakdown voltage of the photodiode is reduced. As such, the number of counted photons is reduced and therefore the pixel device is measured as having an energy level lower than its actual energy level, that is, an energy resolution curve of the pixel device moves leftward.

However, in a pixel device according to example embodiments, as illustrated in FIG. 2, the above problem may be solved by using the voltage supply unit 20 including the voltage storage unit 30 and the voltage adjusting unit 40. If the temperature is increased, a breakdown voltage of the photodiode 10 is reduced and thus a second anode voltage of the photodiode 10 is increased. The first comparator CMP1 compares the second anode voltage to a first anode voltage stored in the voltage storage unit 30. Because the second anode voltage is greater than the first anode voltage, the first transistor TR1 is turned on. Accordingly, the second anode voltage is reduced, and the breakdown voltage is increased, thereby restoring (increasing) the gain of the pixel device.

Figure 9:
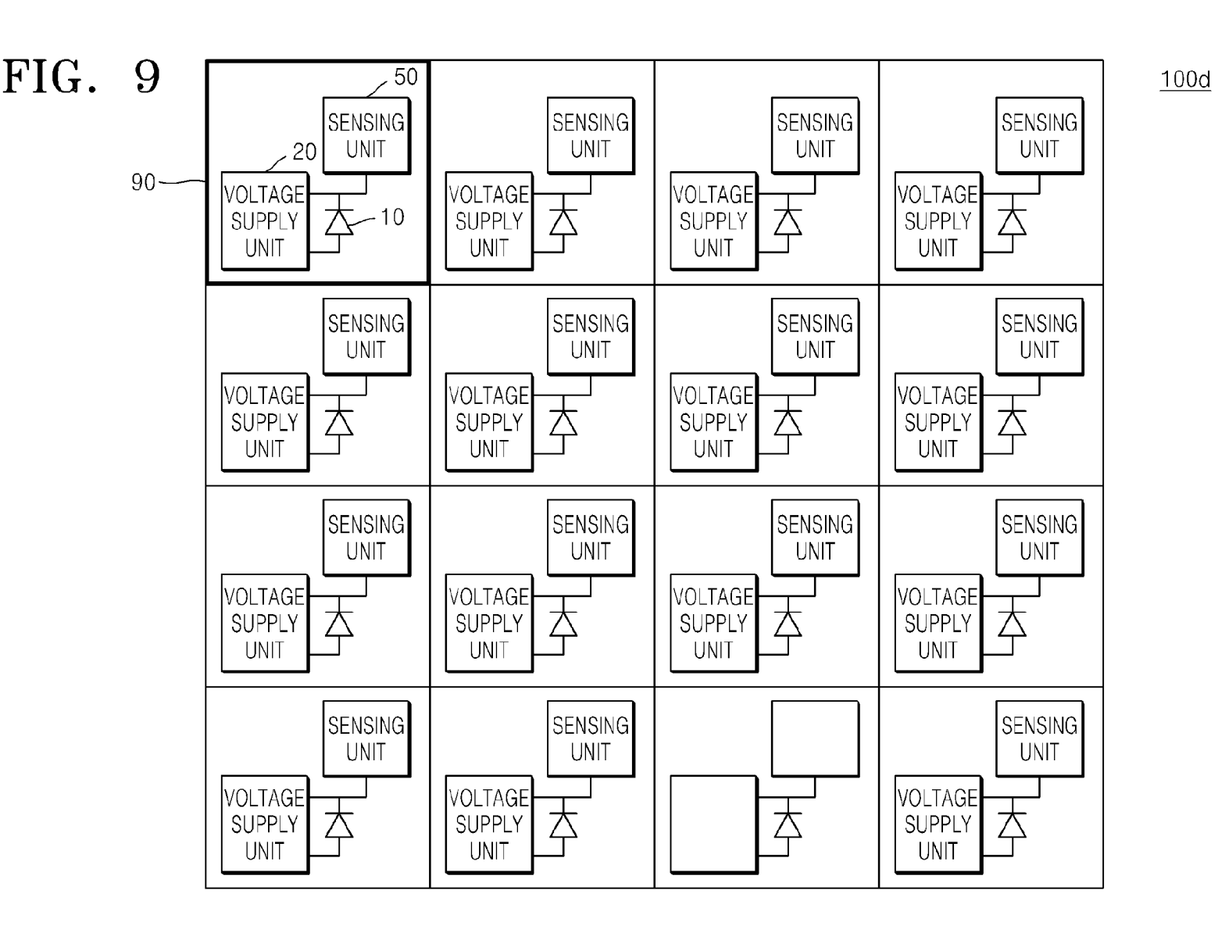
FIGS. 9 and 10 are circuit block diagrams of pixel devices according to other example embodiments.
Figure 10:
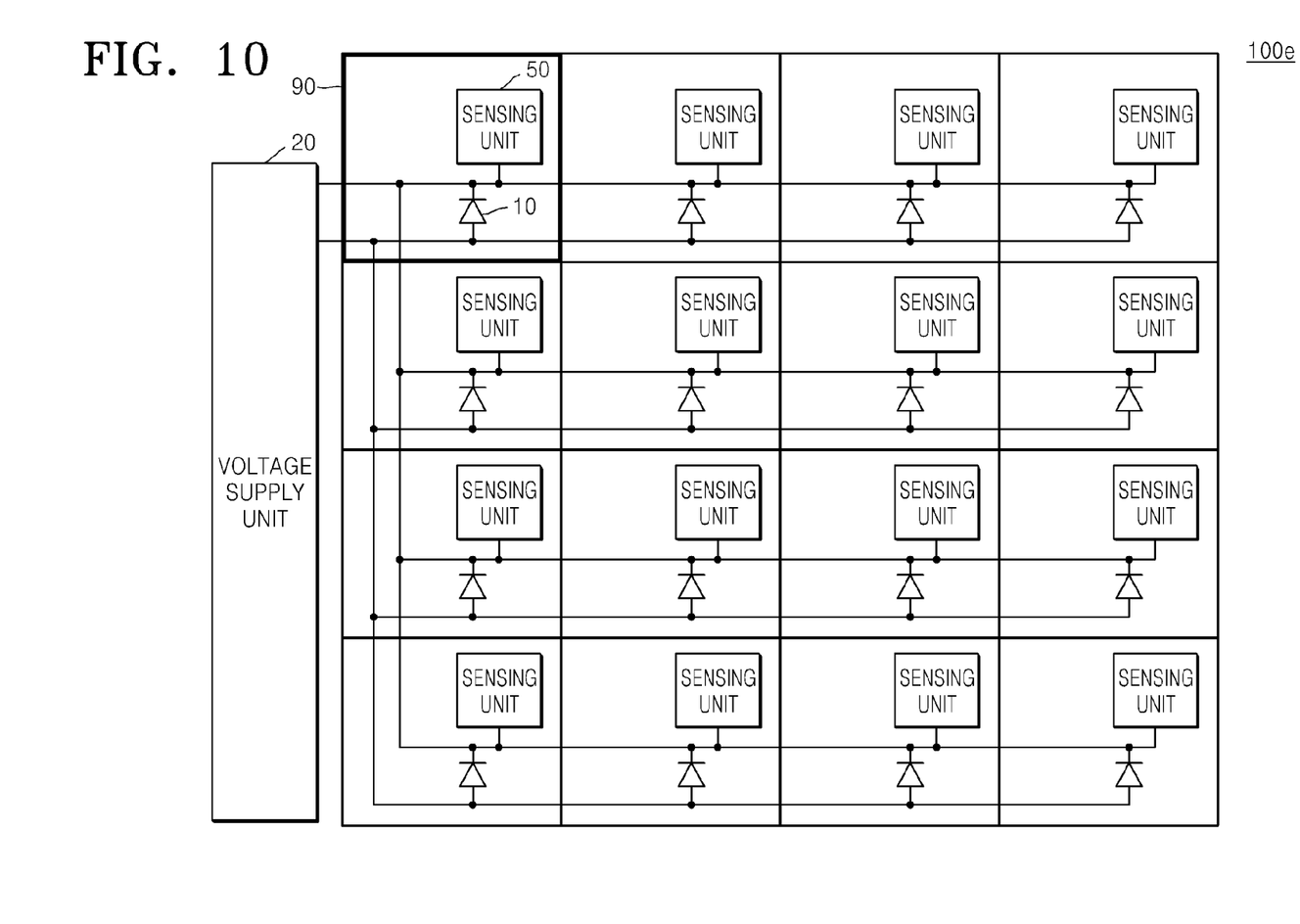

FIGS. 9 and 10 are circuit block diagrams of pixel devices 100d and 100e according to example embodiments. The pixel devices 100d and 100e may be modified from the pixel device 100 illustrated in FIG. 1. Elements described with respect to previous figures will not be further described here.

As described above in relation to FIG. 1, each of the pixel devices 100d and 100e may include a plurality of microcells 90, and each of the microcells 90 may include a photodiode 10 and a sensing unit 50.

A plurality of voltage supply units 20 may be individually included in the microcells 90 as illustrated in FIG. 9. Also, the voltage supply units 20 may be implemented as a single voltage supply unit 20' outside the microcells 90 as illustrated in FIG. 10. In this case, the single voltage supply unit 20' may be connected to the microcells 90 and may apply a breakdown voltage to a plurality of photodiodes 10.

Figure 11:
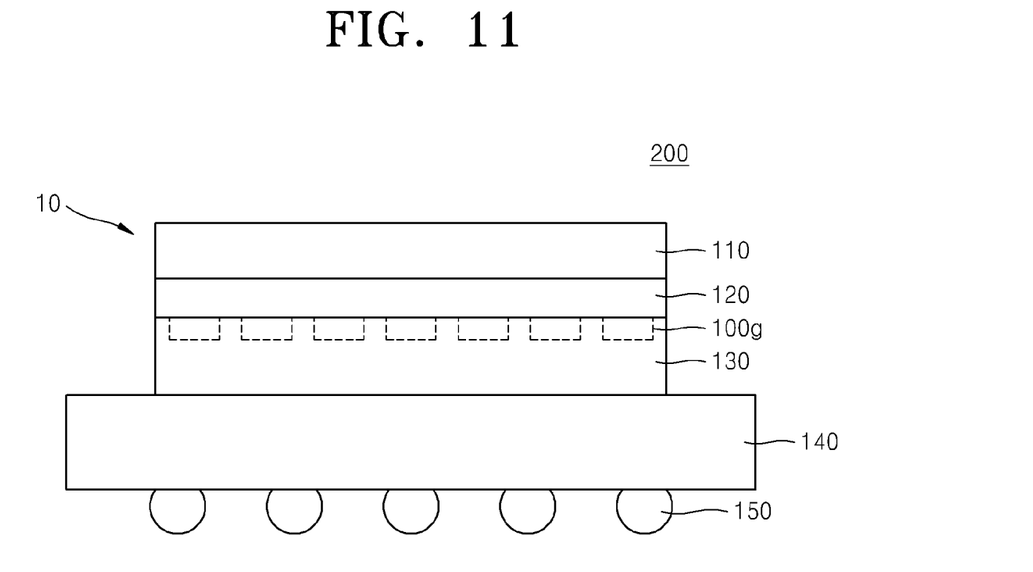
FIG. 11 is a cross-sectional view of a radiation detecting module according to an example embodiment.

FIG. 11 is a cross-sectional view of a radiation detecting module 200 according to example embodiments.

Referring to FIG. 11, the radiation detecting module 200 may include a scintillator 110, a light pipe 120, a semiconductor chip 130, and a PCB 140.

The scintillator 110 may receive radiation, e.g., a gamma ray, and the scintillator 110 may generate photons. The light pipe 120 may be between the scintillator 110 and the semiconductor chip 130, and the light pipe 120 may transfer the photons generated by the scintillator 110 to the semiconductor chip 130.

The semiconductor chip 130 may receive the photons transferred by the light pipe 120, and the semiconductor chip 130 may generate an electrical signal corresponding to the number of photons transferred. The semiconductor chip 130 may include a plurality of pixel devices 100g aligned in the form of an array. Each of the pixel devices 100g may be one of the pixel devices 100d and 100e illustrated in FIGS. 9 and 10. For example, if one pixel device 100e or 100f includes 16 microcells as illustrated in FIGS. 9 and 10, and if the pixel devices 100g are aligned in a 7×7 array on the semiconductor chip 130 as illustrated in FIG. 11, a total of 7×7×16=784 photodiodes 10 may be implemented on the semiconductor chip 130.

The semiconductor chip 130 may be mounted on PCB 140 and the PCB 140 may include a power pin 150 for providing a supply voltage $V_{DD}$ to the pixel devices 100g. For example, the power pin 150 may be a single power pin and the single power pin may be electrically connected to the pixel devices 100g and may provide the supply voltage $V_{DD}$.

Figure 12:
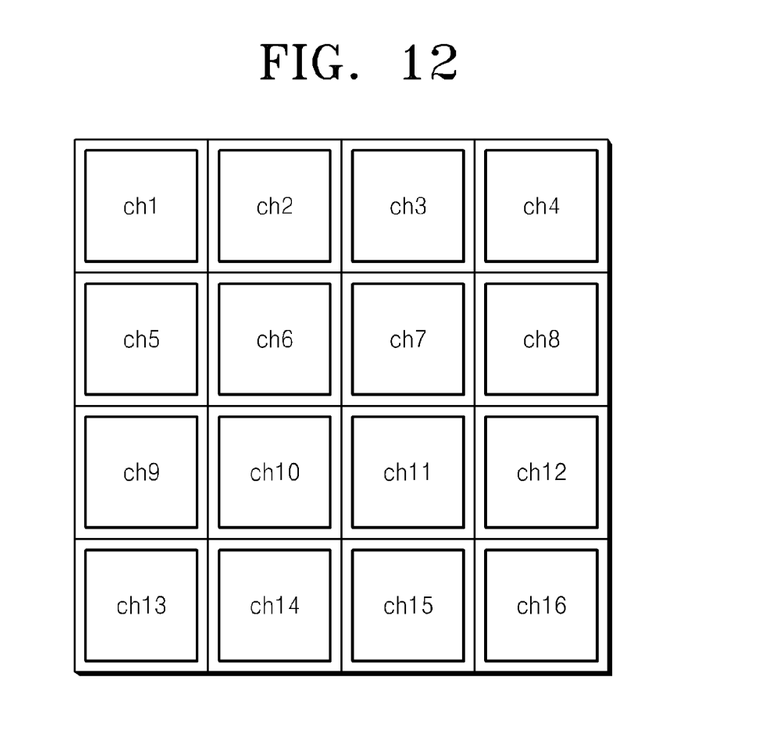
FIGS. 12 and 13 are a plan view and a bottom view of an example conventional radiation detecting module.
Figure 13:
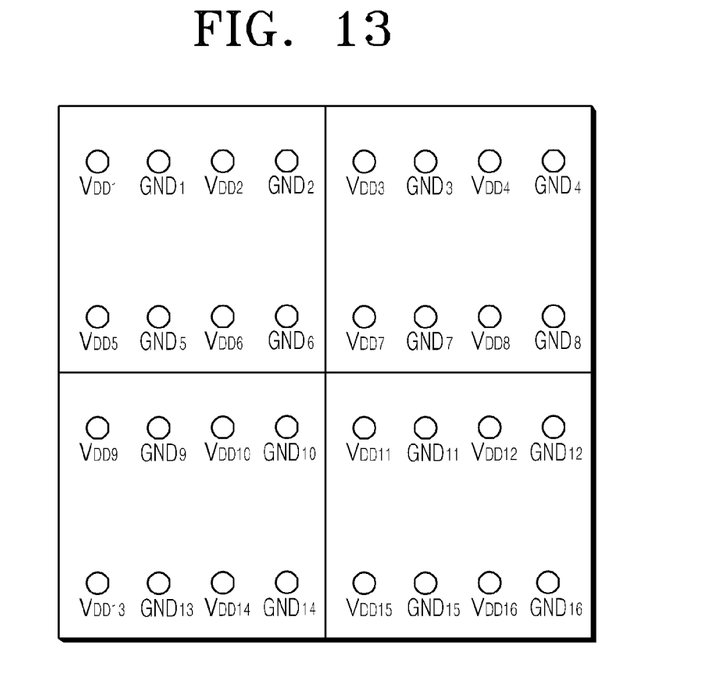

FIGS. 12 and 13 are a plan view and a bottom view of a conventional radiation detecting module. Referring to FIG. 12, a total of 16 pixel devices are implemented. Referring to FIG. 13, 16 power pins $V_{DD1}$ through $V_{DD16}$ and 16 ground pins $GND_1$ through $GND_{16}$ corresponding to the 16 pixel devices are included in a PCB. Because operation of a photodiode may be sensitive to a variation in process conditions or operation temperature, or to stress caused by long-term driving, the 16 power pins $V_{DD1}$ through $V_{DD16}$ should be implemented on the PCB.

However, according to example embodiments, as illustrated in FIGS. 9 through 11, the radiation detecting module 200 may maintain a breakdown voltage of the photodiode 10 by using the voltage supply unit 20, and thus stable operation of the pixel devices 100g may be achieved even by using the single power pin 150.

Figure 14:
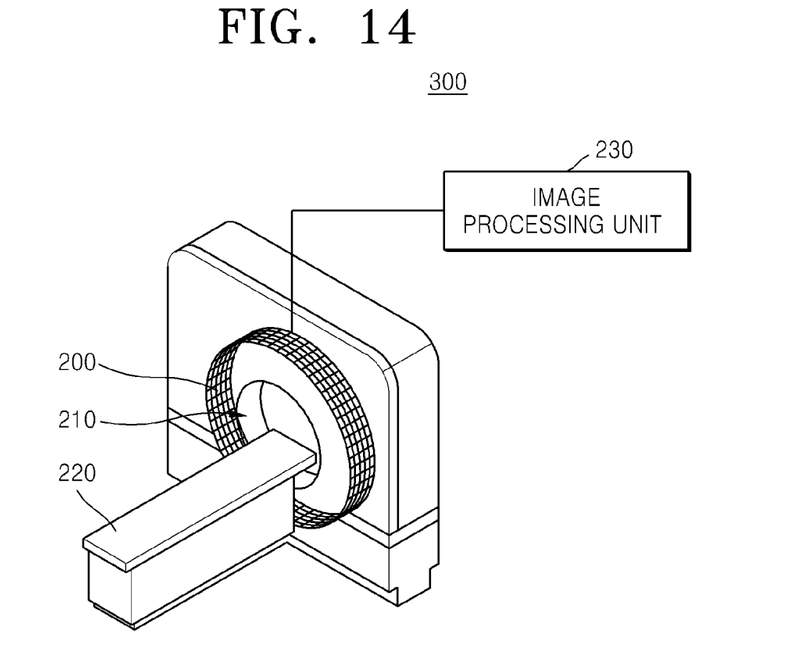
FIG. 14 is a perspective view of a radiation detecting apparatus according to an example embodiment.

FIG. 14 is a perspective view of a radiation detecting apparatus 300 according to example embodiments.

Referring to FIG. 14, the radiation detecting apparatus 300 may include an image region 210, a plurality of radiation detecting modules 200, and an image processing unit 230.

The image region 210 may be a region for accommodating a target object, and may be used to capture an image of the target object. In order to fix the target object, a supporting part 220 may be included in the image region 210. The radiation detecting modules 200 may receive radiation from the target object and may transform the radiation into electrical signals. Each of the radiation detecting modules 200 may be the radiation detecting module 200 illustrated in FIG. 11, and thus repeated descriptions of the radiation detecting modules 200 will not be provided here. The image processing unit 230 may generate the image of the target object based on the electrical signals provided by the radiation detecting modules 200.

A pixel device, and a radiation detecting module and apparatus having the same, according to example embodiments, may maintain a breakdown voltage of a photodiode by using a feedback circuit, e.g., a variation-adaptive closed loop circuit. Accordingly, a variation in operation voltage due to a variation in process conditions or operation temperature, or stress caused by long-time driving may be prevented or reduced, and thus a gain of the photodiode may be maintained. Consequently, an energy resolution of the photodiode may be improved and a dark count may be reduced.

It should be understood that the example embodiments described herein should be considered in a descriptive sense only and not for purposes of limitation. Descriptions of features or aspects within each example embodiment should typically be considered as available for other similar features or aspects in other example embodiments.

What is claimed is:

1. A pixel device comprising:
    at least one photodiode; and
    at least one voltage supply unit configured to apply a voltage to the photodiode, and comprising a voltage storage unit and a voltage adjusting unit,
    wherein, in a precharge mode, the voltage storage unit is configured to store a first anode voltage,
    wherein, in a sensing mode, the voltage adjusting unit is configured to adjust a second anode voltage of an anode of the photodiode to be the same as the first anode voltage stored in the voltage storage unit, and
    wherein the voltage adjusting unit comprises,
        a closed loop circuit,
        a first comparator including,
            a first terminal connected to the voltage storage unit and for receiving the first anode voltage,
            a second terminal connected to the anode of the photodiode and for receiving the second anode voltage, and
            a first output terminal for comparing signals of the first and second terminals and outputting a comparison result, and a transistor including
            a gate connected to the first output terminal of the first comparator,
            a source connected to a ground, and
            a drain connected to the anode of the photodiode.

2. The pixel device of claim 1, wherein the voltage storage unit comprises a capacitor.

3. The pixel device of claim 1, wherein, in the precharge mode, the voltage storage unit is connected to the anode of the photodiode.

4. The pixel device of claim 1, wherein the first anode voltage is a breakdown voltage of the photodiode.

5. The pixel device of claim 1, further comprising:
a quenching unit connected to a cathode of the at least one photodiode, the quenching unit configured to provide a discharge path to allow the at least one photodiode to transition to a quiescent state; and
a readout unit connected to the cathode of the at least one photodiode, the readout unit configured to count transitions of the at least one photodiode.

6. The pixel device of claim 1, wherein the voltage supply unit further comprises:
a first switch connected between the anode of the photodiode and the voltage storage unit, and wherein the first switch is turned on in the precharge mode and is turned off in the sensing mode.

7. The pixel device of claim 6, wherein the voltage supply unit further comprises:
a second switch connected between the voltage storage unit and the voltage adjusting unit, and
wherein the second switch is turned off in the precharge mode and is turned on in the sensing mode.

8. The pixel device of claim 1, wherein the voltage adjusting unit further comprises:
a third switch connected between the gate of the transistor and the first output terminal of the first comparator,
wherein the third switch is turned off in the precharge mode and is turned on in the sensing mode.

9. The pixel device of claim 8, wherein the voltage supply unit further comprises:
a second comparator including,
a third terminal connected to a cathode of the at least one photodiode;
a fourth terminal for receiving a reference voltage; and
a second output terminal for comparing signals of the third and fourth terminals and outputting a comparison result; and
a fourth switch connected between the gate of the transistor and the second output terminal of the second comparator,
wherein the fourth switch is turned on in the precharge mode and is turned off in the sensing mode.

10. The pixel device of claim 1, wherein
the pixel device includes a plurality of microcells,
the at least one photodiode comprises a plurality of photodiodes, and
the plurality of photodiodes are individually comprised in the plurality of microcells.

11. The pixel device of claim 10, wherein the at least one voltage supply unit comprises a plurality of voltage supply units, and
wherein the plurality of voltage supply units are individually comprised in the plurality of microcells.

12. The pixel device of claim 10, wherein the at least one voltage supply unit is a single voltage supply unit, and
wherein the single voltage supply unit is connected to the plurality of microcells and is configured to apply a voltage to the plurality of photodiodes.

13. A radiation detecting module comprising:
a scintillator for receiving radiation and generating photons; and
a plurality of pixel devices configured to receive the photons generated by the scintillator,
wherein each of the plurality of pixel devices includes,
at least one photodiode, and
at least one voltage supply unit configured to apply a voltage to the photodiode, and comprising a voltage storage unit and a voltage adjusting unit,
wherein, in a precharge mode, the voltage storage unit is configured to store a first anode voltage,
wherein, in a sensing mode, the voltage adjusting unit is configured to adjust a second anode voltage of an anode of the photodiode to be the same as the first anode voltage stored in the voltage storage unit, and
wherein the voltage adjusting unit comprises,
a closed loop circuit,
a first comparator including,
a first terminal connected to the voltage storage unit and for receiving a first anode voltage,
a second terminal connected to the anode of the photodiode and for receiving the second anode voltage, and
a first output terminal for comparing signals of the first and second terminals and out-putting a comparison result, and
a transistor including,
a gate connected to the first output terminal of the first comparator,
a source connected to a ground, and
a drain connected to the anode of the photodiode.

14. The radiation detecting module of claim 13, further comprising;
a printed circuit board (PCB) for mounting a semiconductor chip, the PCB including at least one power pin for providing a supply voltage to the plurality of pixel devices,
wherein the plurality of pixel devices are integrated on the semiconductor chip in the form of an array.

15. The radiation detecting module of claim 14, wherein,
the at least one power pin is a single power pin, and
the single power pin is electrically connected to and provides a supply voltage to the plurality of pixel devices.

16. The radiation detecting module of claim 13, wherein, in the precharge mode, the voltage storage unit is connected to the anode of the photodiode.

17. A radiation detecting apparatus comprising:
an image region for accommodating a target object to capture an image of the target object;
a plurality of radiation detecting modules surrounding the image region, configured to receive radiation from the target object, and configured to transform the radiation into electrical signals; and
an image processing unit configured to generate the image of the target object based on the electrical signals,
wherein
each of the radiation detecting modules includes,
a scintillator configured to receive a radiation and generating photons; and
a plurality of pixel devices configured to receive the photons generated by the scintillator,
each of the plurality of pixel devices includes,
at least one photodiode, and
at least one voltage supply unit configured to apply a voltage to the photodiode, and including a voltage storage unit and a voltage adjusting unit,
wherein, in a precharge mode, the voltage storage unit is configured to store a first anode voltage, and wherein, in a sensing mode, the voltage adjusting unit is configured to adjust a second anode voltage of an anode of the photodiode to be the same as the first anode voltage stored in the voltage storage unit, and wherein the voltage adjusting unit comprises,
- a closed loop circuit,
- a first comparator including,
    - a first terminal connected to the voltage storage unit and for receiving a first anode voltage,
    - a second terminal connected to the anode of the photodiode and for receiving the second anode voltage, and
    - a first output terminal for comparing signals of the first and second terminals and outputting a comparison result, and
- a transistor including,
    - a gate connected to the first output terminal of the first comparator,
    - a source connected to a ground, and
    - a drain connected to the anode of the photodiode.

18. The radiation detection apparatus of claim 17, wherein, in the precharge mode, the voltage storage unit is connected to the anode of the photodiode.

* * * * *